United States Patent
Lechner et al.

(10) Patent No.: US 9,103,753 B2
(45) Date of Patent: Aug. 11, 2015

(54) TEM-LAMELLA, PROCESS FOR ITS MANUFACTURE, AND APPARATUS FOR EXECUTING THE PROCESS

(75) Inventors: Lorenz Lechner, Ulm (DE); Ute Kaiser, Ulm (DE); Johannes Biskupek, Ulm (DE)

(73) Assignee: Carl Zeiss Microscopy GmbH (DE)

( * ) Notice: Subject to any disclaimer, the term of this patent is extended or adjusted under 35 U.S.C. 154(b) by 759 days.

(21) Appl. No.: 13/193,578

(22) Filed: Jul. 28, 2011

(65) Prior Publication Data

US 2012/0189813 A1    Jul. 26, 2012

(30) Foreign Application Priority Data

Jul. 30, 2010   (DE) .......................... 10 2010 032 894

(51) Int. Cl.
*G01N 1/28*    (2006.01)
*G01N 1/32*    (2006.01)
(Continued)

(52) U.S. Cl.
CPC .. *G01N 1/28* (2013.01); *G01N 1/32* (2013.01); *H01J 37/3056* (2013.01); *H01J 37/20* (2013.01); *H01J 2237/201* (2013.01);
(Continued)

(58) Field of Classification Search
CPC .............. B23B 3/30; G01N 1/32; G01N 1/28; H01N 37/31745
See application file for complete search history.

(56) References Cited

U.S. PATENT DOCUMENTS

| 4,128,765 A | 12/1978 | Franks |
| 5,472,566 A | 12/1995 | Swann et al. |

(Continued)

FOREIGN PATENT DOCUMENTS

| CN | 1715863 A | 1/2006 |
| CN | 101131909 A | 2/2008 |

(Continued)

OTHER PUBLICATIONS

Lechner et al. "Improved Focused Ion Beam Target Preparation of (S)TEM Specimen", Microsc. Microanal., doi:10.1017/S1431927611012499.*

(Continued)

*Primary Examiner* — Nicole Ippolito
*Assistant Examiner* — James Choi
(74) *Attorney, Agent, or Firm* — Alston & Bird LLP

(57) ABSTRACT

A process for manufacturing a TEM-lamella includes mounting (51) a plate shaped substrate having a thickness in a support, manufacturing (53) a first, strip-shaped recess on a first side of the substrate under a first angle to the support by means of a particle beam, and manufacturing (55) a second strip-shaped recess on a second side of the substrate under a second angle to the support by means of a particle beam, such that the first and the second strip-shaped recess mutually form an acute or right angle, and between them form an overlap region of lesser thickness. The lamella has a thicker rim region and a thinner central region, with a first strip-shaped, recess on a first side of the lamella and a second strip-shaped recess on a second side of the lamella, wherein the first and the second strip-shaped recess mutually form an acute or right angle, and between them form an overlap region having a thickness of below 100 nm. An apparatus for executing the process or manufacturing the lamella includes a lamella support pivotable about a transverse axis and a longitudinal axis inclined, to the vertical direction, a device for rotating about the longitudinal axis, and stop means for limiting a tilt of the lamella support about the transverse axis.

11 Claims, 8 Drawing Sheets

(51) Int. Cl.
*H01J 37/305* (2006.01)
*H01J 37/20* (2006.01)

(52) U.S. Cl.
CPC ............... *H01J 2237/20207* (2013.01); *H01J 2237/31745* (2013.01); *Y10T 428/24479* (2015.01)

(56) References Cited

U.S. PATENT DOCUMENTS

| | | | |
|---|---|---|---|
| 6,080,991 A * | 6/2000 | Tsai | 250/492.21 |
| 6,194,720 B1 | 2/2001 | Li et al. | |
| 6,855,938 B2 | 2/2005 | Preikszas et al. | |
| 7,002,152 B2 | 2/2006 | Grunewald | |
| 2005/0236587 A1 | 10/2005 | Kodama et al. | |
| 2006/0011867 A1 | 1/2006 | Kidron et al. | |
| 2006/0017016 A1 | 1/2006 | Tappel | |
| 2006/0054820 A1 | 3/2006 | Kim et al. | |
| 2006/0261270 A1 | 11/2006 | Burkhardt et al. | |
| 2008/0042059 A1 | 2/2008 | Tashiro et al. | |
| 2008/0099695 A1 | 5/2008 | Sugizaki | |
| 2008/0258056 A1 | 10/2008 | Zaykova-Feldman et al. | |
| 2009/0119807 A1 * | 5/2009 | Man et al. | 850/18 |
| 2010/0006754 A1 | 1/2010 | Zhang et al. | |
| 2010/0032567 A1 | 2/2010 | Maclou Botman et al. | |
| 2010/0032581 A1 | 2/2010 | Grosse et al. | |
| 2010/0090108 A1 | 4/2010 | Hoeche | |
| 2010/0276607 A1 | 11/2010 | Wanzenboeck et al. | |
| 2014/0110577 A1 * | 4/2014 | Lechner | 250/307 |
| 2014/0353497 A1 * | 12/2014 | Demarest et al. | 250/307 |

FOREIGN PATENT DOCUMENTS

| | | |
|---|---|---|
| CN | 101625302 A | 1/2010 |
| DE | 695 06 583 T2 | 7/1999 |
| DE | 103 44 643 A1 | 4/2005 |
| DE | 10 2006 023 768 A1 | 11/2007 |
| DE | 10 2008 052 006 A1 | 4/2010 |
| DE | 10 2009 008 166 A1 | 9/2010 |
| JP | 10132714 A | 5/1998 |
| JP | 11132922 A | 5/1999 |
| JP | 2000035391 A | 2/2000 |
| JP | 2002333412 A | 11/2002 |
| JP | 2003 166 918 A1 | 6/2003 |
| JP | 2003166918 A | 6/2003 |
| JP | 2004047315 A | 2/2004 |
| JP | 2004286486 A | 10/2004 |
| JP | 2004311700 A | 11/2004 |
| JP | 2007115706 A | 5/2007 |
| JP | 2008185338 A | 8/2008 |
| JP | 2008-261891 A | 10/2008 |
| JP | 2010025682 A | 2/2010 |
| JP | 2010091562 A | 4/2010 |
| JP | 2012168002 A * | 9/2012 |

OTHER PUBLICATIONS

Lechner, "TEM Sample Preparation using Focused Ion Beams: Fundamental Problems and Solutions", http://www.tem.agh.edu.pl/ESTEEM2School2013/main/wp-content/uploads/12_Preview-of-Abstract-4sgtem.pdf.*

Mikko Paalanen: "Annual Report 2009", Reports of the Low Temperature Laboratory, AALTO University, Apr. 1, 2010, pp. 1-119.

Lechner, L: "Focused Ion Beam for Rapid Prototyping: A fast road towards graphene electronics", Lorenz Georg Lechner web site, May 25, 2009, pp. 1-42.

Partial European search report dated Nov. 15, 2011 from parallel European patent application No. 11 006 234.6.

Office Action dated Oct. 10, 2014 from parallel Chinese patent application No. 201110318890.7. (with English language translation thereof).

Office action dated Apr. 30, 2013 in German patent application No. 10 2010 064 462.5, 6 pp., with English translation, 4 pp.

Office Action in German patent application No. 10 2010 032 894.4 dated Mar. 24, 2011 (with English-language translation).

Extended European search report dated Feb. 1, 2012 from parallel European patent application No. 11 006 234.6, 14pp.

Office Action dated Jun. 16, 2015 in the parallel Japanese patent application No. 2011-167687.

* cited by examiner

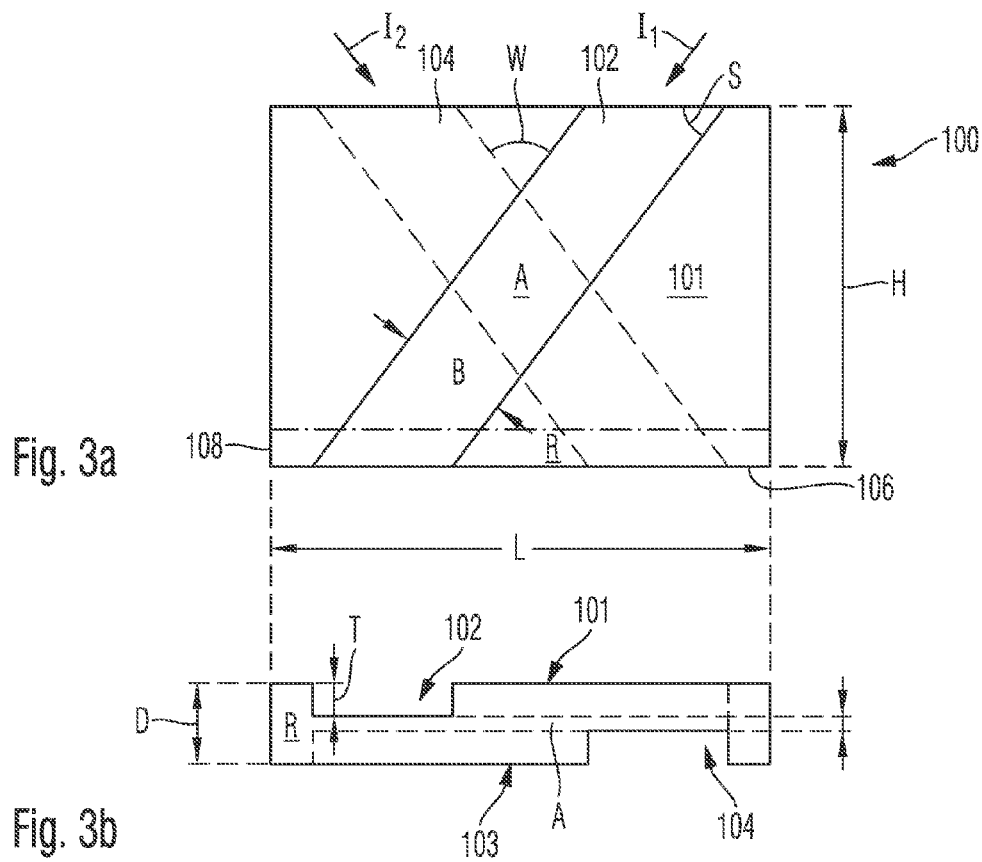
Fig. 3a
Fig. 3b
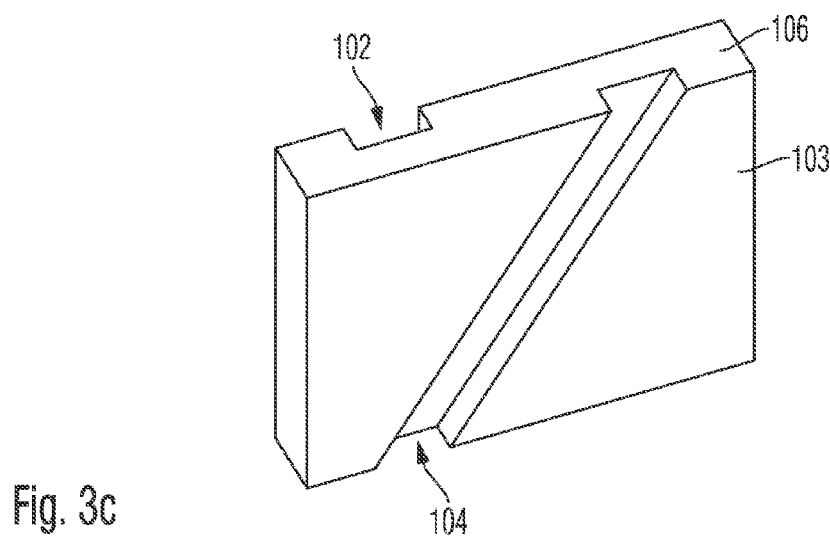
Fig. 3c

TEM-LAMELLA, PROCESS FOR ITS MANUFACTURE, AND APPARATUS FOR EXECUTING THE PROCESS

CROSS-REFERENCES TO RELATED APPLICATIONS

The present application claims priority of Patent Application No. 10 2010 032 894.4, filed Jul. 30, 2010 in Germany, entitled "TEM-LAMELLA, PROCESS FOR ITS MANUFACTURE, AND APPARATUS FOR EXECUTING THE PROCESS", the content of which is hereby incorporated by reference in its entirety.

FIELD

The invention relates to a material sample (TEM-"lamella") suitable for transmission electron microscopy (TEM) studies and in particular a HRTEM-lamella (HR=high resolution), a process for its manufacture, and an apparatus for executing the process.

Transmission electron microscopic (TEM) analysis is one of the most important analysis tools in semiconductor electronics, in part because of its resolution of down to and below 0.1 nm. The preparation of suitable TEM-samples, however, is complicated, because only ultrathin samples ("lamellae") can be used for the highest resolution TEM analysis methods mentioned above. In particular, preparation with a focused ion beam (FIB) has proven suitable, as in this manner, spatially precisely defined cross sections through the substrate to be inspected may be prepared.

BACKGROUND

One process for the preparation of TEM-lamellae is described in the patent application DE 10 2009 008 166 A1, the content of which is incorporated herein by reference in its entirety. According to this application, a protective strip is generated on the substrate surface, and then the substrate material to both sides of the protective strip is removed by means of an ion beam. A plate of the substrate material remains standing between the two troughs formed in this manner, and can then be separated at its periphery from the residual substrate and can be lifted out of the substrate by means of a micromanipulator, wherein the structures of interest are located in the lifted-out plate. A similar process for providing a material plate having a thickness of 5-100 nm is known from the published patent application DE 103 44 643 A1.

However, these generally rectangular material plates are either too thick, or too fragile for high resolution analysis. In patent document U.S. Pat. No. 7,002,152, a preparation method for a partly post-thinned material sample for high resolution electron microscopic studies is described.

This known process is found unsatisfactory in respect of the quality of the material samples (lamellae) so obtained, in particular for high resolution electron microscopy.

The invention assumes that precisely manufactured lamella faces are desirable for such applications.

The known process generates, on the one hand, surfaces which are not sufficiently precisely planar; and on the other hand, the surfaces so generated tend to deform after their manufacture. The present inventors have found that one reason for this is that in the known process, the rim of the sample is weakened. Therefor, any tensions present may distort or bend thin material samples.

SUMMARY

The invention aims at providing an improved sample, an improved process for its manufacture, and am apparatus for implementing the process.

This object is solved by a sample having strip-shaped recesses on both its sides, which are arranged mutually angled, and between which an overlap region of lesser thickness exists. These recesses can be manufactured precisely and stably.

The process for manufacture includes the manufacturing of the two mutually angled recesses with a particle beam. In this manner, the desired precision is achieved. Herein, "angled" is to be understood as a relative orientation in which the longitudinal directions of the recesses, in their projections onto the lamella, include an angle of at least 1° and at most 179°, respectively, in embodiments of minimally 45° and maximally 135°, respectively.

The apparatus for carrying out the process or for manufacturing the sample comprises a lamella support pivotable about a transverse axis, a unit for rotating the support around a longitudinal axis, and a stop for limiting a tilting of the support about its transverse axis. This apparatus provides for a precise orientation of the substrate in relation to the particle beam.

In embodiments, an ion beam obliquely impinging on the substrate is used for manufacturing the recesses. In further embodiments, the recesses are each manufactured contiguously from, one rim of the substrate towards the opposing rim, and in embodiments between different pairs of rims. It is also possible, however, to manufacture the recesses mutually oppositely obliquely to the same rims.

In embodiments, the support is rotated between the manufacturing of the first recess and the manufacturing of the second recess. In still further embodiments, the support is tilted in this step. In this manner, the tilting step can be performed passively, e.g. when the rotation axis is oriented obliquely to the vertical direction. Thereby, the tilting can be accomplished particularly simply, reproducibly and little prone to error.

The sample, in embodiments, includes a rim portion which is everywhere thicker than a central portion surrounded by the rim portion. Thereby, the stability of the central portion is particularly ascertained.

The apparatus for carrying out the process or for manufacturing the sample, respectively, in embodiments comprises a lamella support rotatable around a transverse axis, and a stop for a tilting of the lamella support around the transverse axis. Around the longitudinal axis, the support is rotatable by means of a device, wherein the longitudinal axis is inclined to the vertical direction. In embodiments, a gravity driven toothed bar is provided, or a centre of mass of the lamella support is located away from the transverse axis. In this manner, it is achieved that by rotating it around the longitudinal axis inclined to the vertical direction, the support tilts into the opposite pivot position. Furthermore, in embodiments a particle beam source and guide are provided, suitably an ion beam source and guide. In addition, an electron beam source and guide may be provided for studying the lamella so prepared. The ion and electron beam guides, respectively, provide beams mutually inclined. Suitably, the direction of the trans-verse axis is approximately perpendicular to the surface plane of the supported lamella.

BRIEF DESCRIPTION OF THE DRAWINGS

The forgoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

FIGS. 3a-c show an exemplary TEM-lamella in plan view, in side view and in perspective view;

DETAILED DESCRIPTION OF EXEMPLARY EMBODIMENTS

Figure 1:
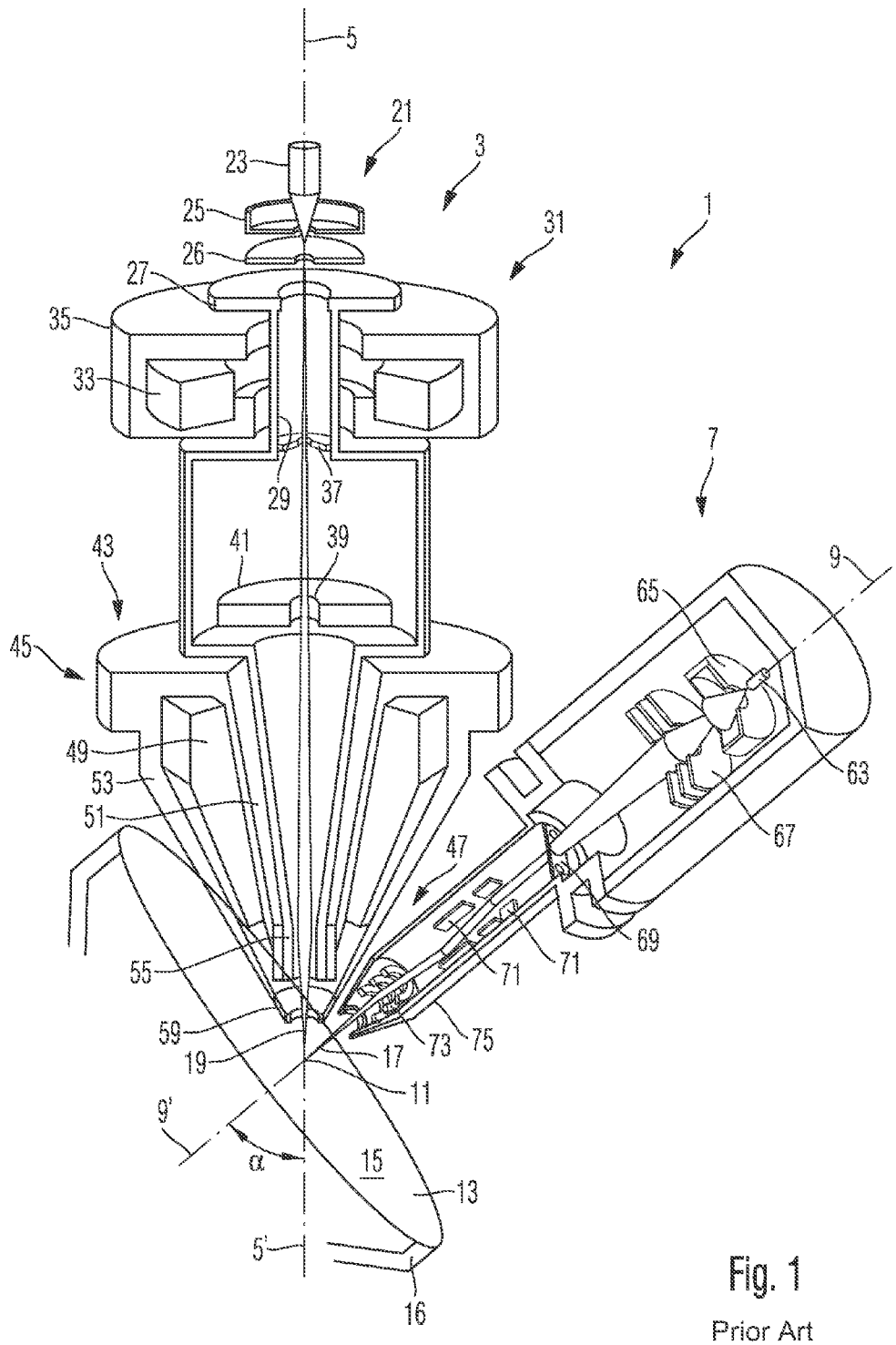
FIG. 1 shows a conventional ion beam preparation system with an electron beam system.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

FIG. 1 shows, in perspective view and schematically, a particle optical assembly 1 for explaining embodiments of the present invention. The particle optical assembly comprises an electron microscopy system 3 with a main axis 5 and an ion beam preparation system 7 with a main axis 9. The main axes 5 and 9 of the electron microscopy system 3 and the ion beam preparation system 7, respectively, intersect at a position 11 under an angle α, which can assume values of e.g. 45° to 55°, so that an object 13 to be inspected having a surface 15 in a region around the position 11 can both be worked on along the main axis 9 of the ion beam preparation system 7 with the emitted ion beam 17, and can be inspected with an electron beam 19 emitted along a main axis 5 of the electron microscopy system 3. For supporting the object, a schematically indicated support 16 is provided, which can position the object 13 in respect of distance from, and orientation to the electron microscopy system. To this end, the electron microscopy system 3 comprises an electron source 21 for generating the primary electron beam 19, which source is shown schematically to include a cathode 23 and an anode 27 as well as a suppressor electrode 25 arranged there between and an extractor electrode 26 arranged spaced apart. Further, the electron microscopy system 3 comprises an accelerator electrode 27, which passes into a beam tube 29 and transects a collimator assembly 31, shown schematically by a ring coil 33 and a yoke 35. After passing through the collimator assembly 31, the primary electron beam transects a pin hole aperture 37 and a central hole 39 in a secondary electron detector 41, whereupon the primary electron beam 19 enters into an objective lens 43 of the electron microscopy system 3. The objective lens 43 for focusing the primary electron beam 19 comprises a magnetic lens 45 and an electrostatic lens 47. The magnetic lens 45 comprises, in the schematic illustration of FIG. 1, a ring coil 49, an inner pole shoe 51 and an outer pole shoe 53. The electrostatic lens 47 is formed by a lower end 55 of the beam tube 29, the inner lower end of the outer pole shoe 53 and a ring electrode 59 conically tapered towards the position 11 at the sample. The objective lens 43, which is shown schematically in FIG. 1, may have a structure as explained in more detail in U.S. Pat. No. 6,855,938, included herein by reference.

The ion beam preparation system 7 comprises an ion source 63 with an extraction electrode 65, a collimator 67, a variable aperture 69, deflector electrodes 71 and focusing lenses 73 for generating the ion beam 17 emanating from a casing 75 of the ion beam preparation system 7. The longitudinal axis 9' of the support 16 is inclined to the vertical direction 5', which is this case corresponds to the angle α between the directions 5 and 9 of the particle beams. The directions 5' and 9' need not coincide with the directions 5 and 9 of the particle beams, however, and also the angle enclosed between them need not match the angle α between the particle beams.

Figure 2A:
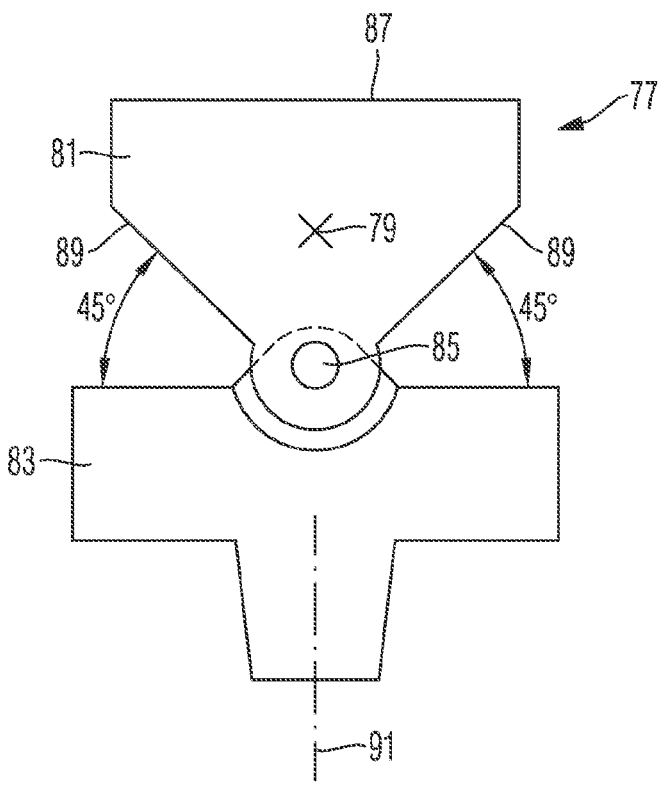
FIG. 2a shows a lamella support according to the invention.

In FIG. 2a, a lamella support 77 according to the invention is shown. One or more of such lamella supports 77 may be mounted on the support 16 of FIG. 1 by means of inserts 83, or may replace those. The lamella support 77 is pivotable around an axis parallel to its longitudinal axis, e.g. in that the support 16 is adapted to be rotatable around its own longitudinal axis 91.

Figure 2B:
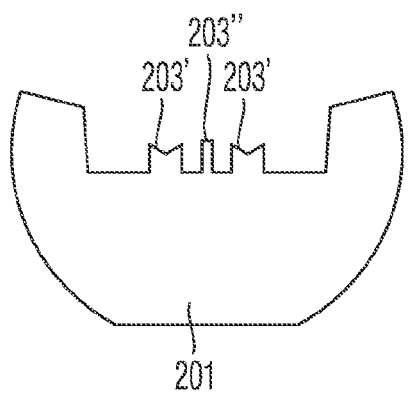
FIG. 2b shows a known structure for mounting the material sample to the lamella support.

The lamella support 77 has a transversely oriented pivot axis 85, which is arranged with a certain distance from the centre of mass 79 of the lamella support 77. The pivot axis 85 is inclined, i.e. forms an angle different from 0° and 180° (e.g. by at least 5°) to the longitudinal axis of the lamella support, in embodiments is perpendicular or almost (e.g. to within ±10° or ±5°) perpendicular to this longitudinal axis. The actual lamella holder 87 is located at the pivotably connected part 81 of the lamella support 77 for mounting the lamella 100. At the side of the lamella support 77 facing away from the lamella holder 87, stops 89 are positioned on both sides of the transverse axis 85, which limit the tilting of the lamella support 77 around the transverse pivot axis 85. The stops 89 can be formed as areas, or as points. In the example shown, the stops 89 are formed as stop surfaces inclined by 90° to one another, and by 45° each to the longitudinal axis 91. An auxiliary structure shown in detail in FIG. 2b is mounted on the lamella holder 87, and the actual material sample is mounted in turn on this auxiliary structure. Such auxiliary structures are commercially available as Omniprobe® Lift-Out Grids from Ted Pella, Inc., Redding Calif., USA. Such auxiliary structures and similar ones e. g. according to the patent application DE 103 44 643 A1 mentioned above, on the one hand comprise an enlarged-area sheet portion 201 made of e.g. copper, molybdenum or molybdenum-coated copper, by which they can be grabbed with normal manipulators (e.g. tweezers) and can be fixed to the lamella, holder 87; on the other hand, comprise one or more filigree extensions at which the comparatively tiny material sample can be supported (e.g. by adhesion). The example shown in FIG. 2b has two broader extensions 203' and between them, one narrower "post" 203".

Figure 4:
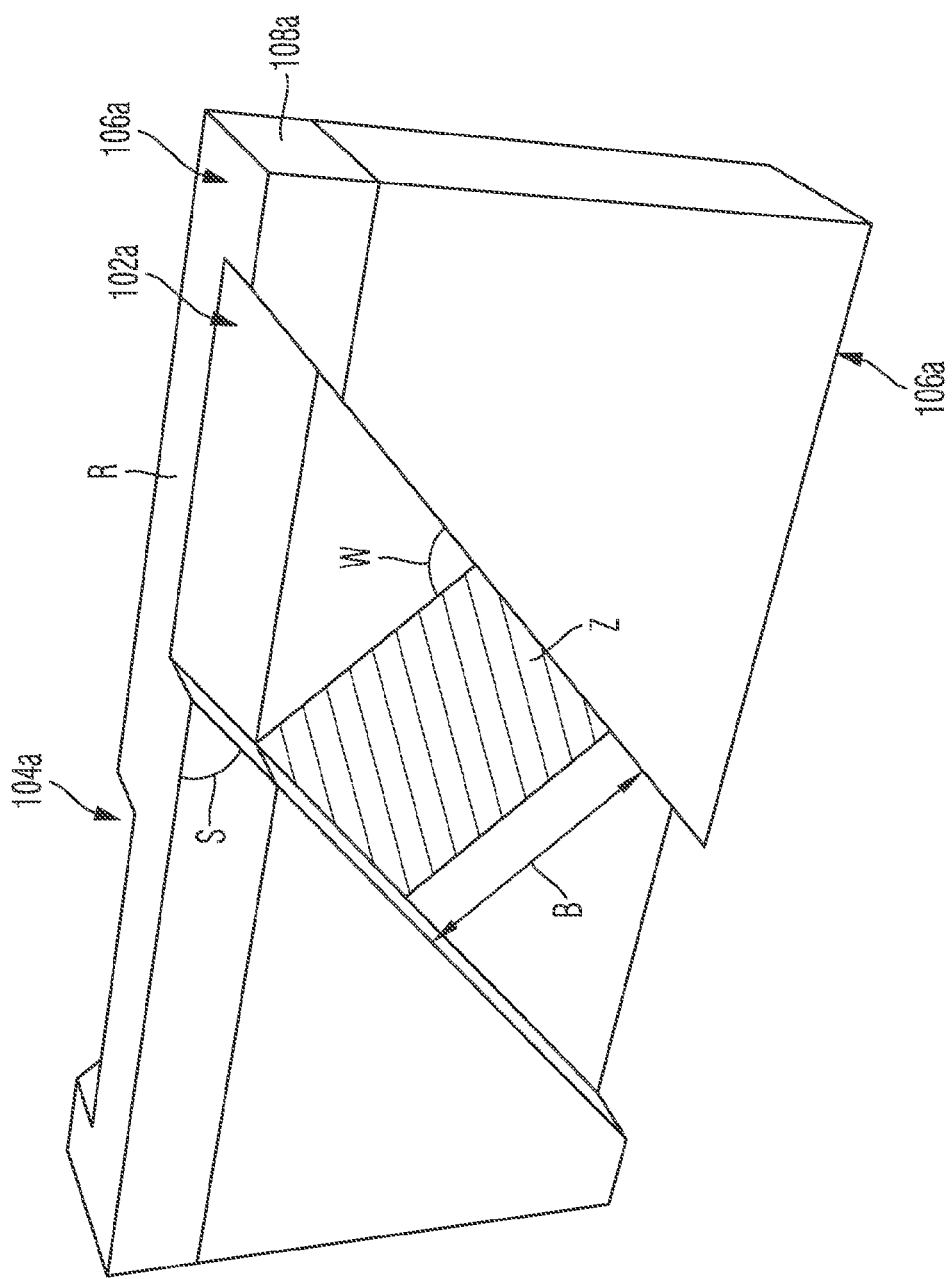
FIG. 4 shows another exemplary TEM-lamella in perspective view.
Figure 5A:
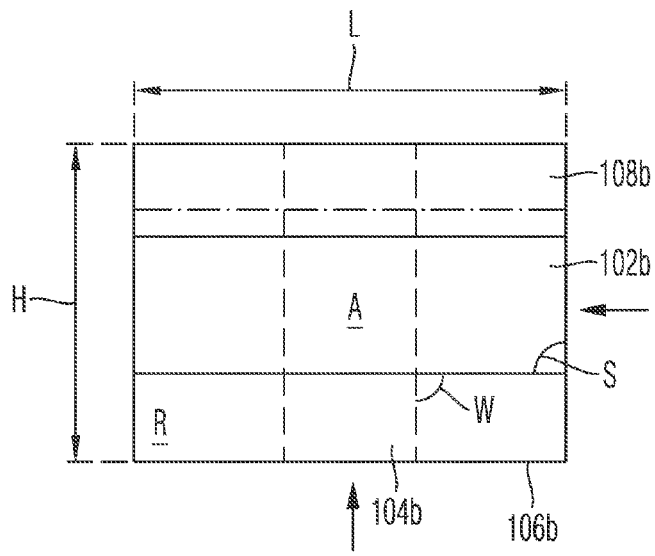
FIGS. 5a,b show another exemplary TEM-lamella in plan view and in perspective view.
Figure 5B:
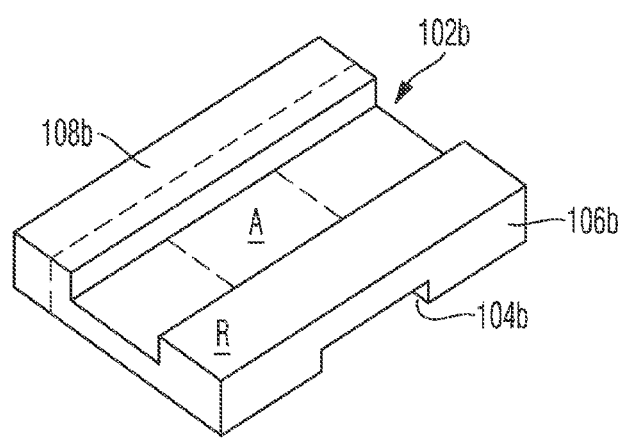

In preparing the lamella 100 (ref. FIGS. 3a to 3c), an ion beam (indicated by an arrow $I_1$) is irradiated, onto one of the flat sides 101 of the substrate, e.g. under a low angle of 1° to 3° to the surface, and the substrate material is removed in a strip of e.g. 1-5 µm width W and a depth. T of almost half the substrate thickness D. In the example, the recess 102 is made to extend over the entire length of the substrate; in other embodiments, the removing process is stopped, before the longitudinal extension of the recess 102 reaches the rim 106 of the substrate on the opposite side. At that position, e.g. a lamella protection layer 108 can be positioned. After completing the first recess 102, the support 16 is rotated together with the insert 83 of the lamella support 77. Because its longitudinal axis 91 is inclined to the vertical direction, the lamella support 77 tilts at a certain rotational position (namely when the transverse axis 85 is positioned in a vertical plane) into the opposing pivot position and thereby pivots the supported substrate 100 such that same disposes its other flat side 103 to the ion beam source, and does so in a different angular orientation. Subsequently, on the other flat side 103 of the substrate a second strip-like recess 104 is manufactured in a similar manner as the first. Because of the tilting of the lamella support 77 between the two manufacturing steps, the guidance of the ion beam need not be changed; nevertheless, the back-side recess 104 is made at an angle W with respect to the front-side recess 102. In the embodiment of FIGS. 5a and 5b the one recess 102b is made approximately parallel to an existing lamella protection layer 108b, and the other recess 104b is made approximately perpendicular thereto (i.e., at an about right angle W), and thereby between those substrate rims 106b not transected by the first recess 102b. In other embodiments (according to FIG. 4), both recesses 102a, 104a are made between the same substrate rims 106a, but under angles S opposed to one another, which oblique angles S are not necessarily, but suitably of equal size. The minimal value for the edge angle S, and thereby the maximal value for the intersection angle W follows from the ratio of height H to length L of the substrate 100 taking into account the width B of the recess. In this embodiment, an almost right angle W between the two recesses 102a is 104a achieved, so that an almost quadratic, relatively large area central region A results. As particularly well discernible from FIG. 3b, in the embodiments shown with recesses 102, 104 of equal depth, the rim portion R is everywhere at least half as thick as the substrate.

Figure 6:
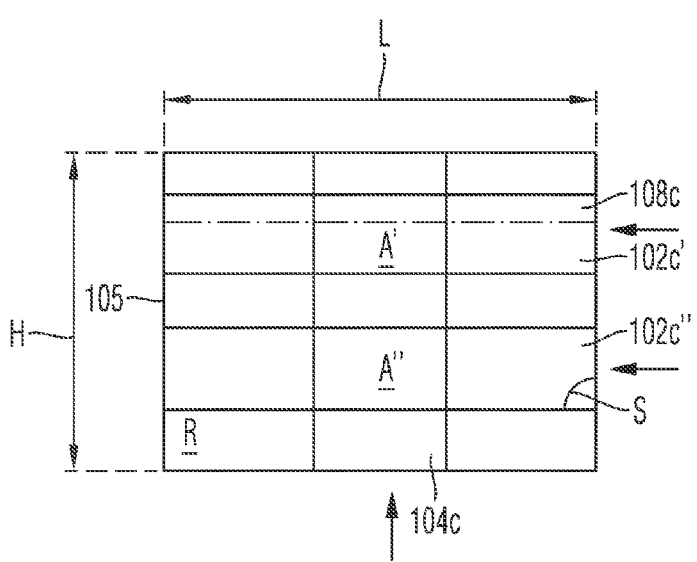
FIG. 6 shows another exemplary TEM-lamella in plan view.

In the further embodiment according to FIG. 6, on one side of the sample plural parallel recesses 102c', 102c'' are shown, one of which extends into the protection layer 108c at the former wafer surface. Thereby, a structure very close to the wafer surface can be examined. Together with the recess 104c on the opposing flat side, in this example two spaced apart central regions A' and A'' are thinned to the same or different thickness suitable for TEM-purposes. Thereby, in the center a strip 105 of the substrate material remains, i.e. more of the reinforcing and stiffening material, as if only a single, accordingly wider recess had been manufactured. In addition, the ion beam operation time for removing the strip 105 is saved.

Generally, the material samples may have outer dimensions of minimally 5 µm×20 µm×0.1 µm (height H×length L×thickness D) to maximally 1 mm×1 mm×0.5 mm, wherein in embodiments, ranges of 10 µm to 20 µm for the height H, 15 µm to 30 µm for the length L and 1 µm to 5 µm for the thickness D are typical. Independently thereof, the material samples may deviate from the rectangular plate shape and e.g. may vary in thickness from one rim region to the opposite rim region, in other words form a wedge shape. The strip-shaped front-side and back-side recesses suitably do not extend inclined to one another in the depth dimension, so that the central region has a uniform thickness.

Figure 7A:
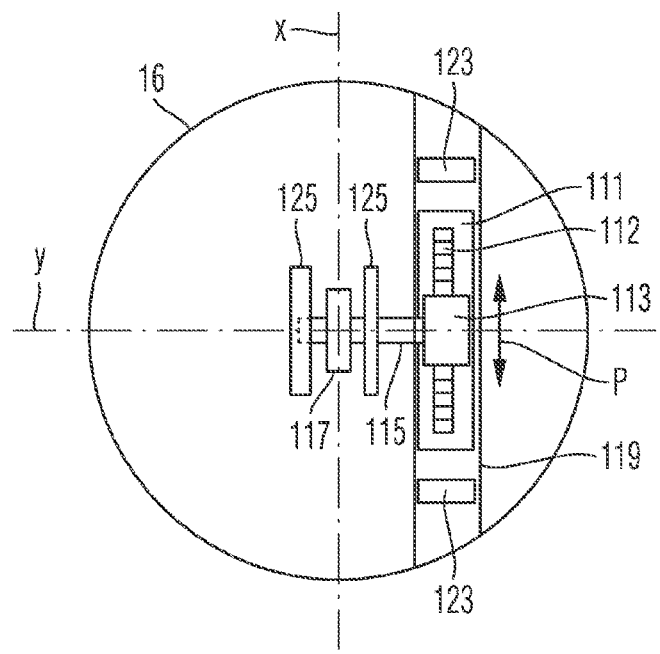
FIGS. 7a-c show another exemplary lamella support with a rotation-translation-transducer in plan view and in side views.
Figure 7B:
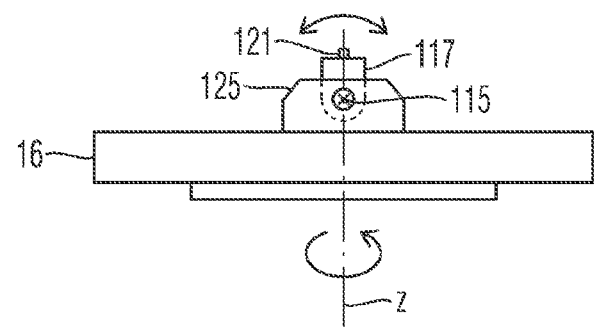
Figure 7C:
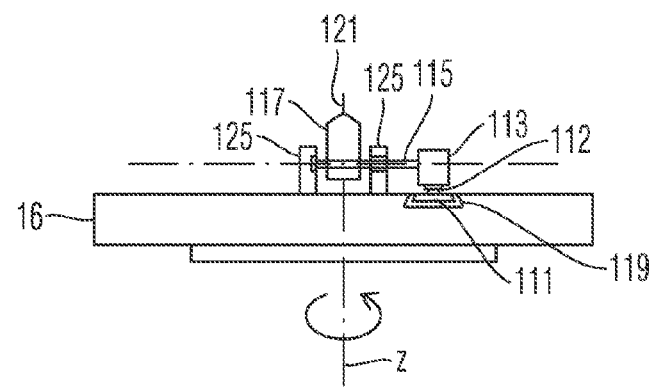

In another embodiment of the lamella support according to FIGS. 7a-c, the pivotal motion of the lamella is made making use of the action of gravity on a linearly movably (along the indicated double arrow P) supported drive element (sled 111), which by means of a toothed bar 112 is in form-based (alternatively, friction-based) engagement with a toothed gear or a toothed sector 113, which in turn is connected by a shaft 115 with the lamella support 117. By rotating the support 16 around the longitudinal axis z (which in operation is inclined to the vertical direction), the guide track 119 of the drive sled 111 is brought into a horizontal orientation and further into an oppositely inclined orientation. Because of the action of gravity, the sled 111 is thereby moved laterally with respect to the support, and this motion in turn causes, by means of the shaft 115 of the toothed bar drive, an angular displacement of the lamella support 117. In this manner, the supported substrate 121 can be moved into the desired orientation relative to the ion beam for working its surface. In this variant, the tilting parts are smaller. The support 16 in this example comprises a guide track 119 for the movable drive element 111; if required, solid lubrication with e.g. graphite can be effected, or a low friction Teflon (PTFE) layer may be provided at the surface of the sled 111 and/or in the guide track 119. The amount of the lateral motion is limited, by stop blocks 123. Furthermore, bearings 125 for the shaft 115 are shown, as well as the position of the axes x and y. Herein, the shaft 115 is parallel to the transverse axis y. The lamella 121 itself is in this example supported, so that the pivot axis is perpendicular to its plane. In operation, the lamella 121 is held at a distance of about 4-6 mm from the electron objective lens.

Suitably, the pivotal assembly is at most 10-20 mm high as measured in the center thereof, and elsewhere is lower, from the base plane of the support 16, in order that the lamella support 117 may not restrict the rotating options for the support 16. In a variant, the pivoting is not made or is not alone made through utilization of gravity, but an additional, e.g. electromechanical actuator is provided, which in response to an initializing signal carries out or supports the pivoting.

Figure 8:
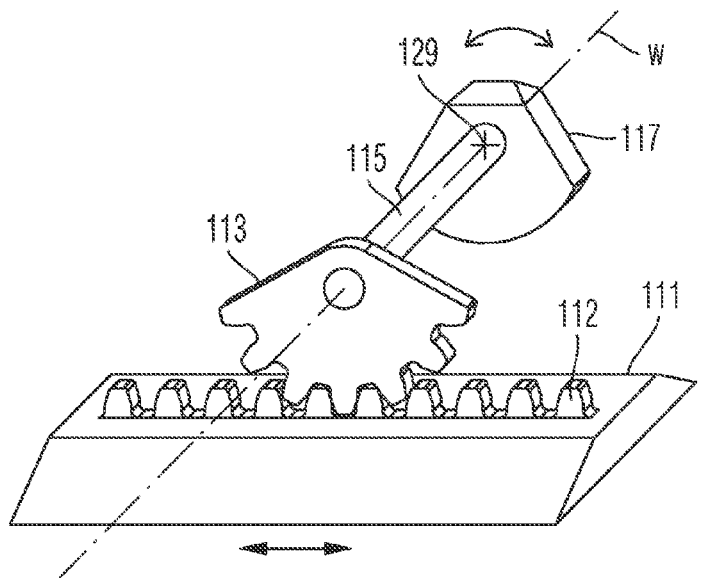
FIG. 8 shows a detailed view of the transducer.

In FIG. 8, an embodiment of an exemplary toothed bar drive is shown, however for simplicity reasons without any bearings. The toothed bar 112 is mounted on the sled 111 movable in the direction of the double arrow, and is in engagement with a toothed sector 113. The driven shaft 115 of same is connected with the lamella support 117, and in this embodiment in such a manner that the centre of mass 129 of the lamella support 117 is near the rotation axis w of the shaft 115, thereby reducing the moment of inertia.

Figure 9:
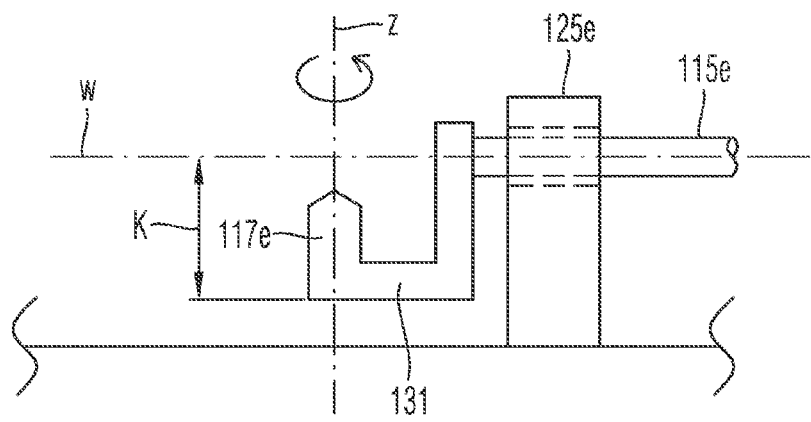
FIG. 9 shows another arrangement of the lamella, support.

In FIG. 9, another variant of the assembly of the lamella support 117e is shown, in which the supported material sample itself is arranged near the extension of the rotational axis w of the shaft 115e. In this arrangement, the supported sample is displaced only minimally when pivoted. Thereby, adjusting the particle beams is simplified. The shaft 115e comprises a cranked end region 131, to which the lamella support 117e is mounted, wherein, the crank K has an amount compensating the size of the support 117e. In this example, the lamella support 117e is located beyond the bearing block 125e, ion order that the particle beams may reach the material probe as unimpeded as possible.

The lamella so manufactured has, in its central region A where the two recesses overlap in their projection onto the lamella plane, a very small thickness of 100 nm or less; even below 20 nm and down to 4 nm are achievable, wherein each of the recesses has a depth of between half the substrate thickness and 10 nm or 2 nm less, respectively. On the other hand, in other embodiments, the depths are different from another (asymmetric), wherein their sum is by 4 to 20 nm or up to 100 nm less than the substrate thickness. In the rim region, the thickness need not be reduced by half the thickness (except in asymmetric recesses). In each of the embodiments shown in FIGS. 3a-c, 4, 5a/b, and 6, a contiguous rim remains which everywhere has at least half the substrate thickness, whereas in the centre region, an extremely thin region A, A' or A", respectively, is formed, which can be trans-luminated with the electron beam system provided for examination purposes. The angle formed between both the recesses in their projection onto the lamella plane, in the examples shown is about 60° or about 90°, respectively. It is suitable to select this angle as at least 30° or 45° or at most 150° or 135° (supplement angle), respectively, because otherwise, the region of overlap between both recesses becomes rather narrow. In the cases shown, the width of each of the recesses is about 2-3 µm; generally, 1 to 5 µm are suitable. At 90° overlap angle (i.e., perpendicular arrangement) of the recesses, a trans-amination area of 1 to 25 $\mu m^2$ or 4-9 $\mu m^2$ results (FIGS. 4, 5a-b). In the first of the lamellae shown, according to FIG. 3a-c and 4, the recesses extend between the same pair of rims, and in the last according to 5a,b and 6, between different pairs. In the first case according to FIG. 3a, the angle W of overlap is an acute angle. However, in a rectangular substrate, a right angle W can be achieved, when both recesses extend between the longer side edges of the rectangle (FIG. 4). In the other case shown (FIGS. 5a, 6), the angle W is a right angle; however, where desired, an acute angle W can be achieved by manufacturing at least one of the recesses obliquely to the rim of the substrate. By placing one of the recesses parallel to the original outer side edge of the substrate, an observation window can be placed directly under the protection layer (FIG. 6), in order to inspect structures located there. In the embodiment shown, both recesses are made to extend contiguously from rim to rim. It is, however, sufficient to make the recesses extend from one rim to including the observation region A, so that the substrate rim region R is even less weakened as a whole, and still more of the ion beam operation time is saved.

Figure 10:
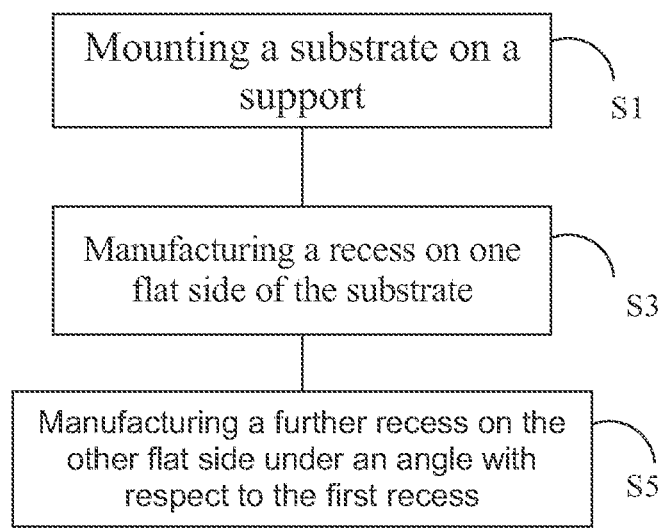
FIG. 10 shows a flow diagram of the inventive process.

In FIG. 10, an embodiment of the process is shown: Initially, the plate shaped lamella substrate is mounted on a support (SI), a strip-shaped recess is formed on one of the flat sides (S3), and a second strip-shaped recess is formed on the other flat side in a manner (S5) that the recesses in their projections on the lamella plane include an acute or right angle, and between them an overlap region of below 100 nm thickness is formed.

This process is particularly suitable for the target preparation, because the sample can be observed electron microscopically while thinning it, and the preparation may therefore be made under visual control. Therefore, the user need not rely on the region of interest (ROD being exactly in the center of the sample. It would be hardly possible to ascertain this, given the tolerances (<5 nm) set by the lamella thickness. Rather, in embodiments, the thinning-process can be stopped when the deepest part of the recess at work reaches the vicinity of the structure of interest (e.g., is within 5 nm thereof), and the second, recess on the opposite side is made correspondingly deeper.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

The invention claimed is:

1. A process for manufacturing a sample for transmission electron microscopic examinations, the process comprising:
    mounting a substrate having a center plane and a thickness measured perpendicularly to the center plane on a support having a mounting plane perpendicular to a mounting direction;
    manufacturing a first strip-shaped recess having a first longitudinal direction on a first side of the substrate under a first angle between the longitudinal direction of the first strip-shaped recess and the mounting direction of the support, using a particle beam; and
    manufacturing a second strip-shaped recess having a second longitudinal direction on a second side of the substrate under a second angle between the second longitudinal direction of the second strip-shaped recess and the mounting direction of the support, using the particle beam, such that the first and second longitudinal directions of the first and second strip-shaped recesses mutually form an acute or right angle, and the first and second recesses form an overlap region of lesser thickness than that of the substrate between them.

2. The process of claim 1, wherein a focused ion beam incident on the substrate inclinedly to the center plane, is used for manufacturing the recesses.

3. The process of claim 1, wherein the first recess is made to extend contiguously from a first rim of the substrate to a second rim of the substrate opposite the first rim, and the second recess is made to extend contiguously from a third rim of the substrate to a fourth rim of the substrate opposite the third rim.

4. The process of claim 1, wherein the support is tilted about an axis between the manufacturing of the first recess and the manufacturing of the second recess, wherein the axis is oriented one of perpendicular and transverse to the center plane.

5. The process of claim 1, wherein the support is rotated about an axis between the manufacturing of the first recess and the manufacturing of the second recess, wherein the axis is oriented one of inclined and parallel to the center plane.

6. The process of claim 5, wherein the rotation axis is oriented one of inclined and perpendicular to the tilt axis.

7. The process of claim 4, wherein the particle beam is used for manufacturing both recesses in the same spatial orientation.

8. The process of claim 5, wherein the particle beam is used for manufacturing both recesses in the same spatial orientation.

9. The process of claim 6, wherein the particle beam is used for manufacturing both recesses in the same spatial orientation.

10. A plate-shaped sample obtained by the process of claim 1, the plate-shaped sample having a thicker rim region and at least one thinner central region, with at least one first strip-shaped recess on a first flat side of the sample and a second strip-shaped recess on a second flat side of the sample, wherein the at least one first recess and the second recess, in projection onto the flat sides, mutually form an acute or right angle, and between them form an overlap region having a thickness of below 100 nm.

11. The sample of claim 10, wherein the rim region is everywhere thicker than the central region.

* * * * *

UNITED STATES PATENT AND TRADEMARK OFFICE
CERTIFICATE OF CORRECTION

| | | |
|---|---|---|
| PATENT NO. | : 9,103,753 B2 | |
| APPLICATION NO. | : 13/193578 | |
| DATED | : August 11, 2015 | |
| INVENTOR(S) | : Lorenz Lechner et al. | |

It is certified that error appears in the above-identified patent and that said Letters Patent is hereby corrected as shown below:

Title Page,

"(73) Assignee: Carl Zeiss Microscopy GmbH (DE)"

should read

--(73) Assignees: Carl Zeiss Microscopy GmbH (DE)

Universitaet ULM (DE)--

Signed and Sealed this
Twelfth Day of April, 2016

Michelle K. Lee
*Director of the United States Patent and Trademark Office*